US010278914B2

(12) United States Patent
Pissavini et al.

(10) Patent No.: US 10,278,914 B2
(45) Date of Patent: May 7, 2019

(54) FORMULATION AND METHOD FOR PROMOTING CUTANEOUS UPTAKE OF MOLECULAR OXYGEN BY SKIN

(71) Applicant: Coty Inc., New York, NY (US)

(72) Inventors: Marc Pissavini, Aspremont (FR); Isabelle Hansenne, Westfield, NJ (US); Muriel Pujos, West New York, NJ (US); Dorothee Bernini, Principality of Monaco (MC); Olivier Doucet, Roquebrune Cap Martin (FR)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 15/235,787

(22) Filed: Aug. 12, 2016

(65) Prior Publication Data

US 2017/0042792 A1 Feb. 16, 2017

Related U.S. Application Data

(60) Provisional application No. 62/204,573, filed on Aug. 13, 2015, provisional application No. 62/208,105, filed on Aug. 21, 2015.

(51) Int. Cl.
| | |
|---|---|
| *A61K 36/88* | (2006.01) |
| *A61K 8/97* | (2017.01) |
| *A61Q 19/00* | (2006.01) |
| *A61K 8/49* | (2006.01) |
| *A61K 8/19* | (2006.01) |

(52) U.S. Cl.
CPC ............... *A61K 8/97* (2013.01); *A61K 8/19* (2013.01); *A61K 8/494* (2013.01); *A61Q 19/00* (2013.01); *A61K 2800/58* (2013.01); *A61K 2800/81* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 4,943,433 A * | 7/1990 | Rudov | A61K 8/97 |
| | | | 424/750 |
| 5,871,756 A | 2/1999 | Jeffcoat et al. | |
| 6,060,071 A | 5/2000 | Motitschke et al. | |
| 6,224,872 B1 | 5/2001 | Shibuya et al. | |
| 6,267,973 B1 | 7/2001 | Motitschke et al. | |
| 6,703,536 B2 | 3/2004 | Roe | |
| 6,989,150 B1 | 1/2006 | Golz-Berner et al. | |
| 7,160,560 B2 | 2/2007 | Pinnell | |
| 7,642,079 B2 | 1/2010 | Cayouette et al. | |
| 8,071,139 B2 | 12/2011 | Widgerow | |
| 8,101,202 B2 | 1/2012 | Branham et al. | |
| 8,101,212 B2 | 1/2012 | Koganov | |
| 8,529,952 B2 | 9/2013 | Criere et al. | |
| 8,535,738 B2 | 9/2013 | Collins et al. | |
| 8,663,712 B2 | 3/2014 | Koganov | |
| 8,980,344 B2 | 3/2015 | Gross | |
| 2002/0192245 A1 | 12/2002 | Jensen et al. | |
| 2006/0013845 A1 | 1/2006 | Speron | |
| 2007/0122492 A1 | 5/2007 | Behr et al. | |
| 2009/0068255 A1* | 3/2009 | Yu | A61K 8/0212 |
| | | | 424/450 |
| 2009/0156486 A1 | 6/2009 | Huang et al. | |
| 2009/0169588 A1 | 7/2009 | Beutler et al. | |
| 2011/0151009 A1 | 6/2011 | Golz-Berner et al. | |
| 2011/0195112 A1 | 8/2011 | Orvar et al. | |
| 2011/0305737 A1 | 12/2011 | Alexiades-Armenakas | |
| 2013/0266536 A1 | 10/2013 | Mantyla et al. | |
| 2014/0127286 A1 | 5/2014 | Doucet et al. | |
| 2014/0301960 A1 | 10/2014 | Pujos et al. | |

FOREIGN PATENT DOCUMENTS

| | | |
|---|---|---|
| EP | 1217984 B1 | 12/2004 |
| EP | 2732806 B1 | 5/2015 |
| EP | 2895140 A1 | 7/2015 |
| KR | 1020120024509 A | 3/2012 |
| WO | WO-2014/076055 A1 | 5/2014 |
| WO | WO-2014/195872 A1 | 12/2014 |
| WO | WO-2017/027806 A1 | 2/2017 |

OTHER PUBLICATIONS

"International Application Serial No. PCT/US2016/046775, International Search Report dated Nov. 21, 2016", 3 pgs.
"International Application Serial No. PCT/US2016/046775, Written Opinion dated Nov. 21, 2016", 8 pgs.
Kotaka, Sadao, et al., "Some Observations on the Bleaching Effect of Ethylenediaminetetraacetic Acid on Green Barley Leaves", *Plant Physiol*, vol. 44, (1969), 809-815.
Wang, W., et al., "$O_2$ microsensors for minimally invasive tissue monitoring", *J. R. Soc. Interface*, 1, (2004), 109-117.
"International Application Serial. No. PCT/US2016/046775, International Preliminary Report on Patentability dated Feb. 22, 2018", 10 pgs.

\* cited by examiner

*Primary Examiner* — Christopher R Tate
*Assistant Examiner* — Russell G Fiebig
(74) *Attorney, Agent, or Firm* — Schwegman Lundberg & Woessner, P.A.

(57) ABSTRACT

Inventive embodiments disclosed herein includes a cosmetic formulation. The formulation includes an extract that includes a barley grass exposed to light, the extract having a molecular oxygen partial pressure of at least about 180 mbar and a chlorophyll concentration of about 180 mg/kg.

10 Claims, 4 Drawing Sheets

FORMULATION AND METHOD FOR PROMOTING CUTANEOUS UPTAKE OF MOLECULAR OXYGEN BY SKIN

CLAIM OF PRIORITY

This application claims the benefit of priority of U.S. Provisional Patent Application No. 62/204,573, filed 13 Aug. 2015 and U.S. Provisional Patent Application No. 62/208,105, filed 21 Aug. 2015 the benefit of priority of each of which is claimed hereby, and which applications are incorporated by reference herein in their entireties.

FIELD

Inventive subject matter disclosed herein relates to methods and formulations for promoting cutaneous uptake of molecular oxygen by skin.

BACKGROUND

Barley is one of the oldest cultured plants. It may be the first cereal domesticated, cultivated in the Middle East, around 7000 BC. Traces of barley are found in the Neolithic period. Barley was considered sacred by ancient Greeks. The ancient Egyptians believed that barley was cultivated by the goddess, Isis.

SUMMARY

Inventive embodiments disclosed herein include a cosmetic formulation. The formulation includes an extract that includes a barley grass exposed to light, the extract having a molecular oxygen partial pressure of at least about 180 mbar and a chlorophyll concentration within a range of about 180 mg/kg.

Embodiments also include a method of increasing oxygen in skin cells. The method includes formulating a skin crème or gel with an oily barley extract that includes barley exposed to light, for application to skin. The barley extract also includes the extract having a molecular oxygen partial pressure of at least about 180 mbar and a chlorophyll concentration of about 180 mg/kg.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Figure 3A:
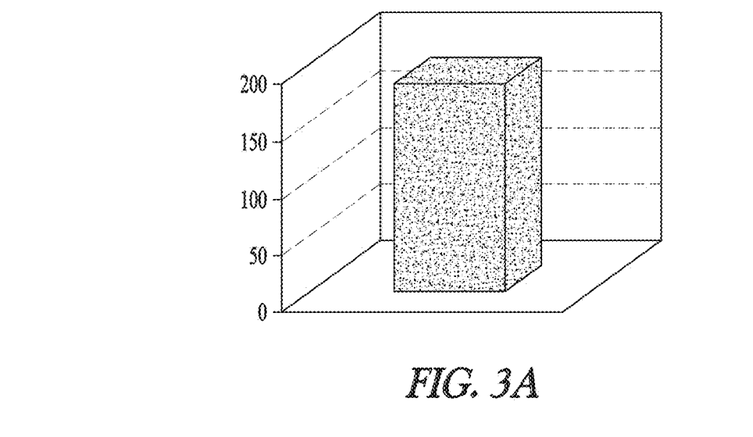
FIGS. 3A-B are graphical views of oxygen and chlorophyll content in a barley extract embodiment of the present invention. A) $O_2$ content in partial pressure measurement by oximeter. B) Chlorophyll.
Figure 3B:
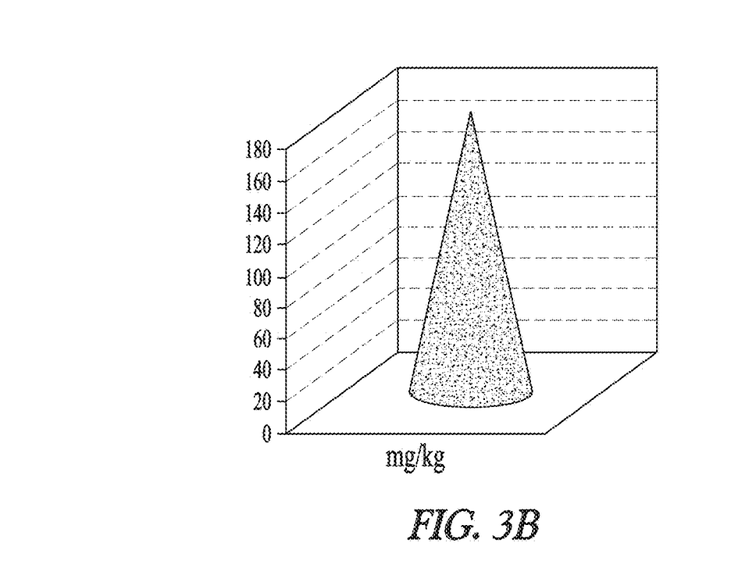

One inventive cosmetic formulation embodiment includes a barley extract formulation having a molecular oxygen content of about 180 mbar partial pressure, as measured by an oximeter and a chlorophyll content of about 180 mg/kg, as shown graphically in FIGS. 3A-B. Barley extract embodiments disclosed herein are obtained from barley grass as a leaf extract. Barley grass contains a large amount of chlorophyll from photosynthesis, a source of natural bioavailable molecular oxygen for the skin. The barley extract embodiments also include this large amount of chlorophyll obtained from photosynthesis. Barley grass for the barley extract embodiments claimed herein is harvested one week after seeding, or when young leaves have a nutritional peak with respect to chlorophyll, before plants begin to produce flowers and seeds. The oily barley extract embodiments include chlorophyll and carotenes. These nutrients, along with molecular oxygen act to generate energy in cells by increasing generation of adenosine triphosphate, ATP, and act to boost production of essential cellular proteins.

Figure 5:
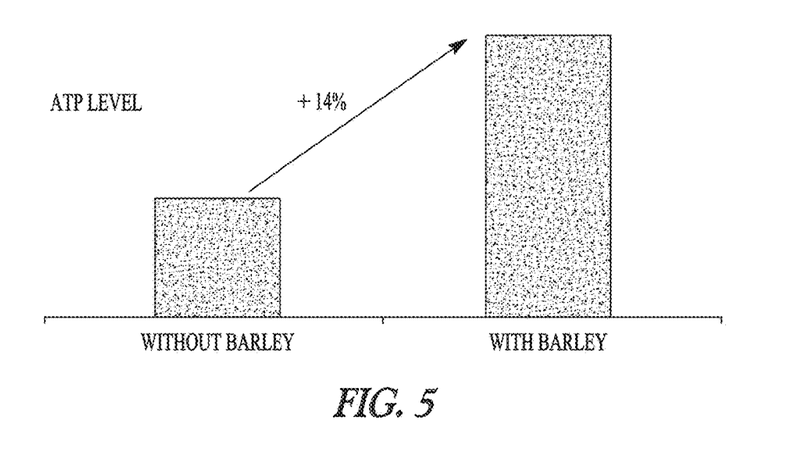
FIG. 5 is a graphical view showing a 14% increase in ATP production for normal human fibroblast cells treated with a barley extract embodiment of the present invention compared to an untreated control fibroblast sample (measurement by bioluminescence).

In one test, a barley extract embodiment of the present invention was exposed to a sample of normal human fibroblasts. An unexposed, control sample was prepared in the same environment and at the same time as the exposed fibroblast sample. ATP concentrations were measured for both the exposed sample and the control sample using bioluminescence. Results are shown in FIG. 5. As can be seen, ATP concentration was fourteen percent greater in the barley extract treated sample compared to the control sample.

Figure 4:
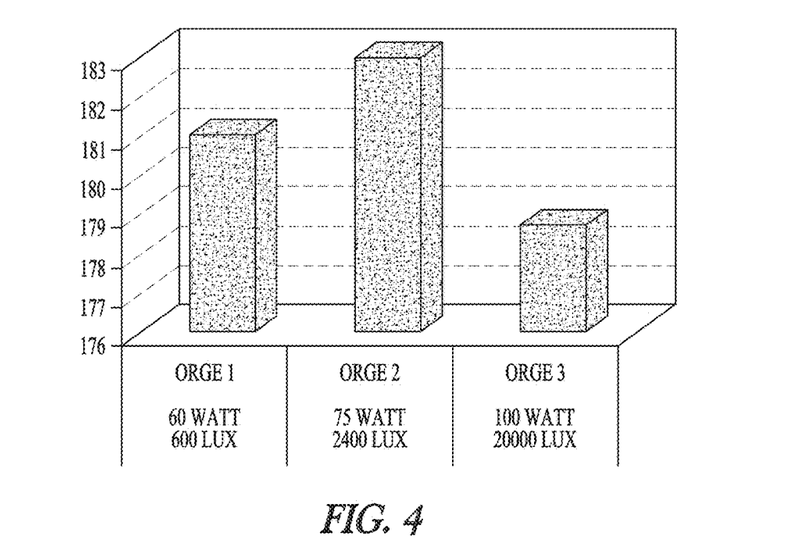
FIG. 4 is a graphical view of oxygen partial pressure at RT in three barley extracts exposed to 60 Watt/600 Lux, 75 Watt/2400 Lux and 1100 Watt/20000 Lux.

The barley employed in the barley extract embodiments was exposed to a 75 Watt, 2400 Lux light source. Testing has also been performed on separate samples using exposure to 60 Watt, 600 Lux and 100 Watt, 20000 Lux light sources, respectively. Results of the testing is shown graphically in FIG. 4. The data shows a partial oxygen pressure of about 180 mbars for barley exposed to 60 Watts/600 Lux; 183 mbars for barley exposed to 75 Watts/2400 Lux and 178 mbars for barley exposed to 100 Watts/20000 Lux. The data shows that the most intense light did not produce barley having the highest oxygen partial pressure. The barley exposed to 75 Watts/2400 Lux produced extract with the highest oxygen partial pressure.

Barley extract embodiments disclosed herein are obtained from barley cultivated under a specific type of lighting. Lighting used to make the barley extract is 2400 Lux, as measured with a luximeter. A Lux is equal to one lumen per square meter.

Figure 1:
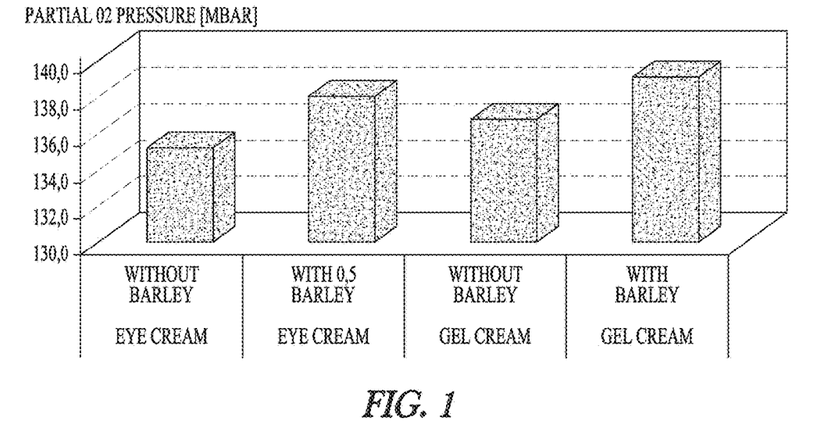
FIG. 1 is a graphical view of the partial pressure in mbar of an eye cream without barley extract and with a barley extract and a gel cream without a barley extract and with a barley extract. Eye cream with 0.5% barley shows an improvement until about 3.0 mbar compared to eye cream without barley after 1 month at room temperature (rt). Gel cream with 0.5% barley shows an improvement until about 2.5 mbar compared to gel cream without barley after 1 month at rt.
Figure 2:
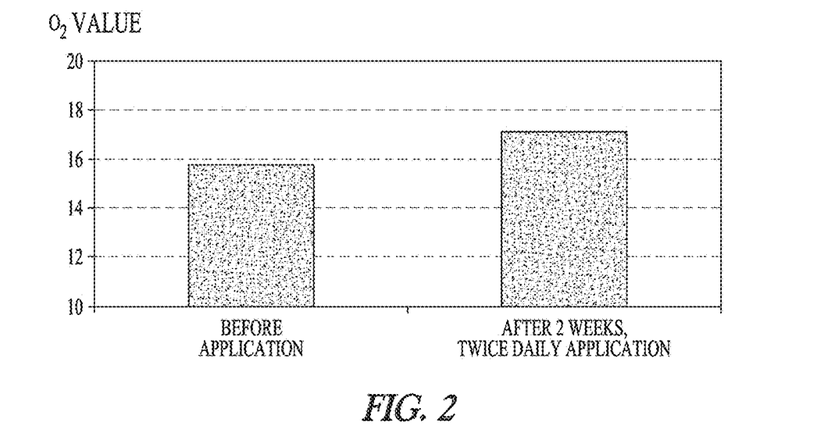
FIG. 2 is a graphical view of oxygen measurements of an exemplary gel crème. Demonstrates improved skin oxygenation (n=9).

It has surprisingly been found that cosmetic formulations made with an oily barley extract having barley exposed to the higher light intensity are rich in chloroplasts and demonstrate an increase in oxygen compared to formulas without the barley extract. Formulations disclosed herein have demonstrated an improved oxygen content exposed to the formulations, as shown in FIGS. 1 and 2. Molecular oxygen from ambient air is absorbed within the skin as a concentration gradient. The gradient is driven by a cutaneous uptake of oxygen and a microcirculation system that transfers molecular oxygen from the barley extract and the atmosphere into the cutaneous and subcutaneous layers of the skin.

Cream containing the barley extract is applied to the exterior surface of skin and aids in the barley extract diffusing into the skin to provide skin with an increased oxygen supply. Creams made with barley extract embodiments increase molecular oxygen concentrations over time. In one example, a gel crème having a partial pressure of molecular oxygen of 112 mbars, initially, had a partial pressure of 107.8 mbars one month later.

All living organisms that depend upon oxygen obtain their energy from a respiratory system where molecular oxygen is reduced to water and energy in the form of ATP. Any living organism requires energy in enough quantity to stay metabolically active, repair and regenerate for cell division. In particular, human cells from skin, directly exposed to sun, are highly dependent upon energy to fight damage and to fight cell deregulation. Cellular energy levels decrease with age and these deficiencies are highly correlated with alteration of human skin structure. This mechanism produces signs of aging.

Oxygen is an essential factor in collagen production. Appropriate molecular oxygen concentration is essential in allowing normal hydroxylation of collagen and accumulation of neo synthesized collagen is increased in tissue with elevated $PO(2)$. When oxygen is brought to fibroblasts, it increases their synthetic capacity.

Oxygen supply by microcirculation and skin oxygen content in the skin depend upon factors like age, sex, and microangiopathic risk. Thus, smokers have a reduced amount of oxygen in their skin. Male subjects in general have lower $PO(2)$ levels than women. In women, $PO(2)$ levels decrease rapidly from ages 30 to 45 and then start increasing again after 50 years. This increase may be linked to changes of skin thickness in relation to hormonal changes and hormonal replacement therapy. Aging is accompanied by an increase of insufficient oxygen supply from capillaries to the tissue.

For some embodiments, the barley extract is combined with other ingredients to relaunch cellular respiration by increasing and improving microcirculation. These other ingredients include caffeine, alpha glycosyl hesperidin and soy protein.

Some formulation embodiments include skin microcirculation boosters. Boosters include caffeine and alpha glycosyl hesperidin, known to boost skin microcirculation. Soy protein extract is used for some embodiments, as a cell respiration booster. The soy protein extract improves the energy level of cells, relaunching cell respiration.

Some formulation embodiments include an anti-pollution complex. The anti-pollution complex includes combination of rpfnn, cyclo amino acid, Tahitian extract and a biotechnology agent.

Some formulation embodiments include an antioxidant complex. The antioxidant complex includes angelica, pongamia, green coffee, green tea, and bitter orange peel. The antioxidant complex neutralizes up to 95% of free radicals responsible for premature aging. The effectiveness of the antioxidant complex is shown in FIG. 2.

Some formulation embodiments include ectoin. Ectoin is a substance produced by halophilic bacteria, such as *ectothiorhodospira halochloris*, which survive and grow under extreme conditions in salt lakes, sea water and saline deserts. Exposed to high dosage of UV radiation, dryness, extreme temperatures and high salinity, these bacteria have managed to adapt to these inhospitable conditions. The cells maintain cell stability by synthesizing ectoin, a cyclo amino acid compatible with the metabolism of the cell, even in high concentrations.

Carbon particles and diesel exhaust significantly increase expression of toxic pathway of cells as well as pro pigmentation pathway and pro aging pathway. Ectoin reduces these increases, helping to limit further toxin production, pollution induced pigmentation and pollution induced aging.

Tahitian extract is a polysaccharide extract obtained from a lagoon on the island of Moorea in French Polynesia. Tahitian extract is a chelator of heavy metals in pollution, in particular, cadmium and lead, which are often present in diesel exhaust, atmospheric pollution and pollutants. On the island of Moorea, a system of ponds provides excellent environmental conditions to develop microbial communities called, Kopara, which produce under stress conditions, exopolysaccharides to protect from external aggression. Tahitian polysaccharide extract biosorbs cadmium and lead.

A biotechnological agent is added to some embodiments of the formulation to boost cell detoxification by boosting autophagy. Autophagy is used by cells for repeated moderate stress or intense stress to eliminate altered proteins that become toxic for the cell and recycle them into amino acids. With age, or when cells are overwhelmed by aggression, the autophagy system can declines. The biotechnological extract boosts autophagy via formation of lysosomes which are a key actor in the autophagic detoxification system and by favoring lc2 synthesis, protein involved in autophagosomes formation. Lysosomes are small bags containing hydrolytic enzymes able to digest macromolecules.

Some formulation embodiments include bisabolol. Bisabolob has a soothing and anti-irritating effect.

Eye formulations disclosed herein include a combination of peptides and a flavonoid to act on three components of puffiness: capillary permeability; lymphatic drainage; and inflammation. Polyphenol, found in citrus, regulates capillary permeability. Dipeptide vallitryptophan limits action of angiotensin converting enzyme, contributing to regulating lymphatic circulation. Palmitoyl oligopeptide acts on firmness and reduces inflammation. Canneine reduces puffiness and dark circles.

One formulation embodiment is a pale green, translucent gel crème which leaves a cool refreshing, light weight and is hydrating after feel.

| Formula Name: | Oxygenating Eye Gel Cream | Formula #: 1 | | Batch Number: | |
|---|---|---|---|---|---|
| # | INCI Name | Raw Material Name | Wet % | Wet Wt | Units |
| | Phase A | Phase A | 74.54% | 1863.50 | g |
| 1 | WATER | WATER, DEIONIZED | 74.54% | 1863.50 | g |
| | Phase B | Phase B | 0.34% | 8.50 | g |
| 2 | ADENOSINE | Adenosine | 0.04% | 1.00 | g |
| 3 | CAFFEINE | Caffeine Anhydrous Powder | 0.30% | 7.50 | g |
| | Phase C | Phase C | 6.10% | 152.50 | g |
| 4 | GLYCERIN | GLYCERINE USP | 0.03 | 75 | g |
| 5 | PENTYLENE GLYCOL | HYDROLITE-5 | 0.03 | 75 | g |
| 6 | DISODIUM EDTA and WATER | Versene Na2 | 0.001 | 2.5 | g |
| | Phase D | Phase D | 0.003 | 7.5 | g |
| 7 | ETHYLENE OXIDE (and) 1,4 DIOXANE (and) ETHYL ACETATE (and) WATER (and) HYDROXYSTEARIC ACID (and) POLYETHYLENE GLYCOL (and) TRIDECETH-6 (and) ACRYLATES/C10-30 ALKYL ACRYLATE CROSSPOLYMER | CARBOPOL ® ULTREZ 21 | 0.003 | 7.5 | g |
| | Phase E | Phase E | 0.004 | 10 | g |
| 8 | AMMONIUM ACRYLOYLDIMETHYLTAURATE/VP COPOLYMER and T-BUTYL ALCOHOL and WATER | Aristoflex AVC/USA | 0.004 | 10 | g |
| | Phase F | Phase F | 0.0345 | 86.25 | g |
| 9 | CETEARYL ALCOHOL and CETEARYL GLUCOSIDE | Montanov 68 | 0.0025 | 6.25 | g |
| 10 | CETYL ALCOHOL | CETYL ALCOHOL | 0.002 | 5 | g |
| 11 | CAPRYLIC/CAPRIC TRIGLYCERIDE | Liponate GC | 0.02 | 50 | g |
| 12 | POLYGLYCERYL-2 DIISOSTEARATE | DERMOL DGDIS | 0.01 | 25 | g |
| | Phase G | Phase G | 0.0024 | 6 | g |
| 13 | WATER | WATER, DEIONIZED | 0.00168 | 4.2 | g |
| 14 | SODIUM HYDROXIDE | Sodium Hydroxide Pellets | 0.00072 | 1.8 | g |
| | Phase H | Phase H | 0.0943 | 235.75 | g |
| 15 | WATER | WATER, DEIONIZED | 0.05 | 125 | g |
| 16 | WATER (and) BUTYLENE GLYCOL (and) *ALTEROMONAS* FERMENT EXTRACT | Exo-P | 0.005 | 12.5 | g |
| 17 | WATER (and) YEAST EXTRACT (and) PHENOXYETHANOL (and) ETHYLHEXYLGLYCERIN | CELLDETOX PX | 0.01 | 25 | g |
| 18 | ECTOIN | RONACARE ECTOIN | 0.0003 | 0.75 | g |
| 19 | HYDROLYZED SOY PROTEIN (and) PHENOXYETHANOL (and) SORBIC ACID | Phylderm Vegetal C2 | 0.005 | 12.5 | g |
| 20 | GLUCOSYL HESPERIDIN | Alpha Glucosyl Hesperidin | 0.001 | 2.5 | g |
| 21 | WATER (and) GLYCERIN (and) HESPERIDIN METHYL CHALCONE (and) STEARETH-20 (and) DIPEPTIDE-2 (and) PALMITOYL TETRAPEPTIDE-7 (and) CHLORHEXIDINE DIGLUCONATE (and) POTASSIUM SORBATE (and) CITRIC ACID (and) SODIUM CITRATE | EYELISS | 0.005 | 12.5 | g |
| 22 | MALACHITE EXTRACT (and) WATER | MALAKITE | 0.008 | 20 | g |
| 23 | GLYCERIN and water and SODIUM HYALURONATE and PENTYLENE GLYCOL and PHENOXYETHANOL | Botanigel 1% PG BCS#11460 | 0.01 | 25 | g |
| | Phase I | Phase I | 0.0145 | 36.25 | g |
| 24 | CAPRYLIC/CAPRIC TRIGLYCERIDE (and) *HORDEUM VULGARE* EXTRACT (and) *ROSMARINUS OFFICINALIS* (ROSEMARY) LEAF EXTRACT | Barley Concentrated Oily Extract Stabilized | 0.005 | 12.5 | g |

-continued

| # | INCI Name | Raw Material Name | Wet % | Wet Wt | Units |
|---|---|---|---|---|---|
| 25 | WATER and GLYCERIN and LECITHIN and ALCOHOL DENAT and *COFFEA ARBABICA* (COFFEE) SEED EXTRACT and *CAMELLIA SINENSIS* LEAF EXTRACT and *PONGAMIA PINNATA* SEED EXTRACT and CITRIC ACID and *ANGELICA ARCHANEGELICA* ROOT EXTRACT and MALTODEXTRIN and *CITRUS AURANTIUM AMARA* (BITTER ORANGE) PEEL EXTRACT and PHENOXYETHANOL and CAPRYLYL GLYCOL and SORBIC ACID and XANTHAN GUM and MAGNESIUM ALUMINUM SILICATE and PEG-8 and *SCEROTIUM* GUM and TOCOPHEROL and ASCORBYL PALMITATE and ASCORBIC ACID | RPF Complex NN DN | 0.001 | 2.5 | g |
| 26 | BISABOLOL and FARNESOL | 600115 Dragosantol 100 | 0.005 | 12.5 | g |
| 27 | PHENOXYETHANOL | PHENOXYETHANOL | 0.0035 | 8.75 | g |
|  | Phase J | Phase J | 0.03 | 75 | g |
| 28 | CYCLOHEXASILOXANE (and) CYCLOPENTASILOXANE (and) CYCLOTETRASILOXANE (and) DIMETHICONE | SILICONE 200/100 | 0.01 | 25 | g |
| 29 | DIMETHICONE and POLYSILICONE-11 | Gransil DM-5 | 0.02 | 50 | g |
|  | Phase K | Phase K | 0.0075 | 18.75 | g |
| 30 | LAURETH-7 (and) WATER (and) C13-14 ISOPARAFFIN (and) POLYACRYLAMIDE | SEPIGEL ™ 305 | 0.0075 | 18.75 | g |
|  | TOTALS: | TOTALS: | 100.00% | 2500.00 | g |

Formula Name: Oxygenating Gel Cream  Formula #: 2  Batch Number:

| # | INCI Name | Raw Material Name | Wet % | Wet Wt | Units |
|---|---|---|---|---|---|
|  | Phase A | Phase A | 74.19% | 741.90 | g |
| 1 | WATER | WATER, DEIONIZED | 72.41% | 724.10 | g |
| 2 | DISODIUM EDTA and WATER | Versene Na2 | 0.10% | 1.00 | g |
| 3 | ADENOSINE | Adenosine | 0.04% | 0.40 | g |
| 4 | ECTOIN | RONACARE ECTOIN | 0.03% | 0.30 | g |
| 5 | GLUCOSYL HESPERIDIN | Alpha Glucosyl Hesperidin | 0.01% | 0.10 | g |
| 6 | CAFFEINE | Caffeine Anhydrous Powder | 0.003 | 3 | g |
| 7 | CARBOMER | CARBOPOL 980 | 0.004 | 4 | g |
| 8 | AMMONIUM ACRYLOYLDIMETHYLTAURATE/VP COPOLYMER and T-BUTYL ALCOHOL and WATER | Aristoflex AVC/USA | 0.004 | 4 | g |
| 9 | METHYL GLUCETH-20 | GLUCAM E20 | 0.005 | 5 | g |
|  | Phase B | Phase B | 0.026 | 26 | g |
| 10 | HYDROGENATED LECITHIN | LECINOL S-10 | 0.006 | 6 | g |
| 11 | GLYCERIN | GLYCERINE USP | 0.02 | 20 | g |
|  | Phase C | Phase C | 0.113 | 113 | g |
| 12 | TOCOPHERYL ACETATE | DO NOT USE - DL-ALPHA TOCOPHERYL ACETATE - USE TRM010503 | 0.0025 | 2.5 | g |
| 13 | CYCLOHEXASILOXANE (and) CYCLOPENTASILOXANE (and) CYCLOTETRASILOXANE (and) DIMETHICONE | SILICONE 200/100 | 0.008 | 8 | g |
| 14 | CETYL ALCOHOL | CETYL ALCOHOL | 0.005 | 5 | g |
| 15 | OCTYLDODECYL NEOPENTANOATE | Elefac 1-205 | 0.0075 | 7.5 | g |
| 16 | POLYSORBATE 80 | Tween 80-LQ-AP | 0.005 | 5 | g |
| 17 | ISODODECANE | PERMETHYL 99A | 0.02 | 20 | g |
| 18 | CAPRYLIC/CAPRIC TRIGLYCERIDE | Liponate GC | 0.02 | 20 | g |
| 19 | CYCLOHEXASILOXANE (and) CYCLOPENTASILOXANE | SILICONE DC 345 | 0.045 | 45 | g |
|  | Phase D | Phase D | 0.0203 | 20.3 | g |
| 20 | BUTYLENE GLYCOL | Butylene Glycol | 0.01 | 10 | g |
| 21 | PENTYLENE GLYCOL | HYDROLITE-5 | 0.01 | 10 | g |
| 22 | O-CYMEN-5-OL | NET-DTB | 0.0003 | 0.3 | g |
|  | Phase F | Phase F | 0.004 | 4 | g |
| 23 | SODIUM HYDROXIDE | Sodium Hydroxide Pellets | 0.0012 | 1.2 | g |
| 24 | WATER | WATER, DEIONIZED | 0.0028 | 2.8 | g |
|  | Phase G | Phase G | 0.03 | 30 | g |

-continued

| | | | | | |
|---|---|---|---|---|---|
| 25 | BIS-PEG-18 METHYL ETHER DIMETHYL SILANE and BHT | DOW CORNING 2501 | 0.03 | 30 | g |
| | Phase H | Phase H | 0.031 | 31 | g |
| 26 | WATER and GLYCERIN and LECITHIN and ALCOHOL DENAT and *COFFEA ARBABICA* (COFFEE) SEED EXTRACT and *CAMELLIA SINENSIS* LEAF EXTRACT and *PONGAMIA PINNATA* SEED EXTRACT and CITRIC ACID and *ANGELICA ARCHANEGELICA* ROOT EXTRACT and MALTODEXTRIN and *CITRUS AURANTIUM AMARA* (BITTER ORANGE) PEEL EXTRACT and PHENOXYETHANOL and CAPRYLYL GLYCOL and SORBIC ACID and XANTHAN GUM and MAGNESIUM ALUMINUM SILICATE and PEG-8 and *SCEROTIUM* GUM and TOCOPHEROL and ASCORBYL PALMITATE and ASCORBIC ACID | RPF Complex NN DN | 0.001 | 1 | g |
| 27 | WATER (and) BUTYLENE GLYCOL (and) *ALTEROMONAS* FERMENT EXTRACT | Exo-P | 0.005 | 5 | g |
| 28 | WATER (and) YEAST EXTRACT (and) PHENOXYETHANOL (and) ETHYLHEXYLGLYCERIN | CELLDETOX PX | 0.01 | 10 | g |
| 29 | HYDROLYZED SOY PROTEIN (and) PHENOXYETHANOL (and) SORBIC ACID | Phylderm Vegetal C2 | 0.005 | 5 | g |
| 30 | BISABOLOL and FARNESOL | 600115 Dragosantol 100 | 0.005 | 5 | g |
| 31 | CAPRYLIC/CAPRIC TRIGLYCERIDE (and) *HORDEUM VULGARE* EXTRACT (and) *ROSMARINUS OFFICINALIS* (ROSEMARY) LEAF EXTRACT | Barley Concentrated Oily Extract Stabilized | 0.005 | 5 | g |
| | Phase I | Phase I | 0.025 | 25 | g |
| 32 | LAURETH-7 (and) WATER (and) C13-14 ISOPARAFFIN (and) POLYACRYLAMIDE | SEPIGEL 305 | 0.025 | 25 | g |
| | Phase J | Phase J | 0.004 | 4 | g |
| 33 | PHENOXYETHANOL | PHENOXYETHANOL | 0.004 | 4 | g |
| | Phase K | Phase K | 0.002 | 2 | g |
| 34 | FRAGRANCE | FC PH R14-5538 | 0.002 | 2 | g |
| | Phase L | Phase L | 0.0028 | 2.8 | g |
| 35 | Blue 1 0.10% solution | Blue 1 0.10% solution | 0.0006 | 0.6 | g |
| 36 | Yellow 5 0.10% solution | Yellow 5 0.10% solution | 0.0022 | 2.2 | g |
| | TOTALS: | TOTALS: | 100.00% | 1000.00 | g |

Example 1

Part 1:

An eye cream was employed for the test. For one sample of eye cream, 0.5% w/w barley extract was added. For another sample, no barley extract was added. Measurement of oxygen was based upon measurements of partial pressure of oxygen in the two samples. Results are shown in FIG. 1. The eye cream that included the barley extract had an oxygen content about 3.0 mbar more than the oxygen content of the eye cream not containing a barley extract.

Part 2:

A gel cream was employed for the test. For one sample of gel cream, 0.5% w/w barley extract was added. For another sample, no barley extract was added. Measurement of oxygen was based upon measurements of partial pressure of oxygen in the two samples. Results are shown in FIG. 1. The gel cream that included the barley extract had an oxygen content about 2.5 mbar more than the oxygen content of the gel cream not containing a barley extract.

Figure 6:
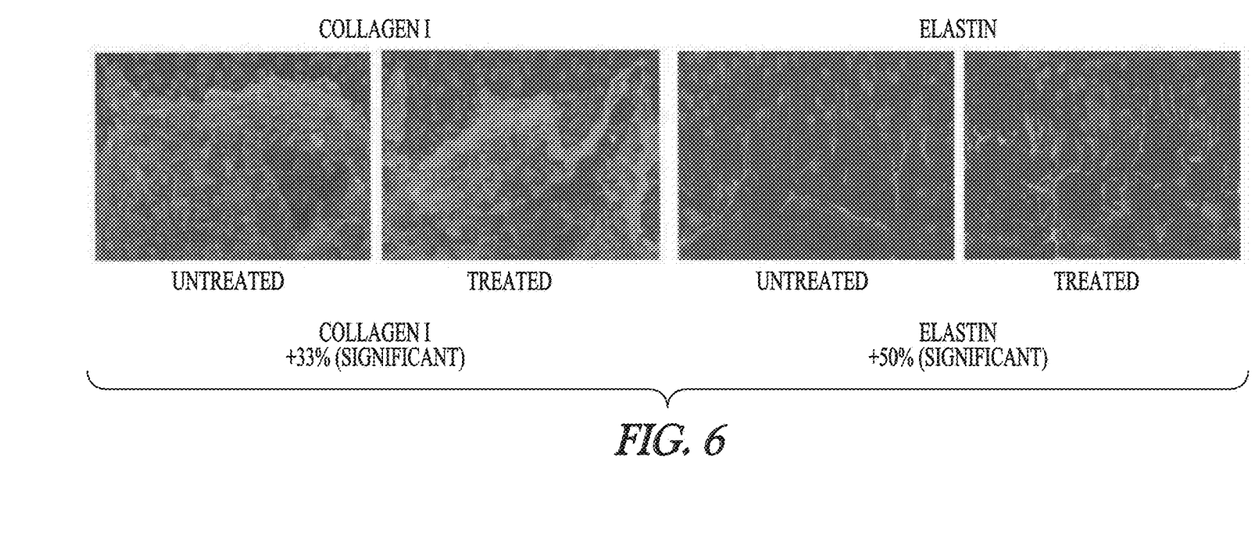
FIG. 6 is a micrographic view of skin biopsy samples treated with a gel crème that includes a barley sample and a gel crème that is free from a barley sample (normal human skin biopsies treated for 11 days).

When the gel crème, including the barley extract was applied to a normal human skin biopsy, Collagen I and elastin showed significant improvement compared to that of a skin cell biopsy that was not treated, as shown in FIG. 6.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed is:

1. A method of increasing oxygen in skin cells of a subject in need thereof comprising topically applying an effective amount of a skin crème or gel formulation comprising a barley (*Hordeum vulgare*) extract to the skin of said subject, wherein the barley extract has a molecular oxygen partial pressure of at least 180 mbar and a chlorophyll concentration of about 180 mg/kg, and wherein the barley extract is obtained by extracting barley leaves that have been cultivated under a 75 Watt, 2400 Lux light source.

2. The method of claim 1, wherein the barley is gluten free.

3. The method of claim 1, wherein the crème or gel formulation comprises:
- a first phase comprising water;
- a second phase comprising adenosine and caffeine;
- a third phase comprising glycerine and pentylene glycol;
- a fourth phase comprising CARBOPOL® Ultrez 21 (acrylates/C10-30 alkyl acrylate crosspolymer);
- a fifth phase comprising acryloyldimethyltaurate/VP copolymer
- a sixth phase comprising caprylic/capric triglyceride;
- a seventh phase comprising water and sodium hydroxide;
- an eighth phase comprising water; the barley extract, and phenoxyethanol,
- a ninth phase comprising silicone 200/100;
- a tenth phase comprising SEPIGEL™ 305 (polyacrylamide and C13-14 isoparaffin and laureth-7).

4. The method of claim 1, wherein the formulation further comprises microcirculation boosters.

5. The method of claim 4, wherein the microcirculation boosters comprise hesperidin, alpha glycosyl hesperidin, biostimulating soy protein and/or caffeine.

6. The method of claim 1, wherein the formulation further comprises an anti-pollution shield.

7. The method of claim 1, wherein the formulation further comprises bisabolol.

8. The method of claim 1, wherein the formulation further comprises one or more moisturizers.

9. The method of claim 1, wherein the formulation has a gel consistency.

10. The method of claim 1, wherein the formulation has a cream consistency.

* * * * *